United States Patent
Hyer et al.

(10) Patent No.: US 9,108,021 B2
(45) Date of Patent: Aug. 18, 2015

(54) LOW DRAG, HIGH PRESSURE SEPTUM

(75) Inventors: Daniel Kirk Hyer, Layton, UT (US); Corey Christensen, Salt Lake City, UT (US); Carl Ellis, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 323 days.

(21) Appl. No.: 13/402,133

(22) Filed: Feb. 22, 2012

(65) Prior Publication Data
US 2013/0218082 A1 Aug. 22, 2013

(51) Int. Cl.
*A61M 25/00* (2006.01)
*A61M 25/06* (2006.01)
*A61M 39/00* (2006.01)
*A61M 39/06* (2006.01)

(52) U.S. Cl.
CPC ....... *A61M 25/0097* (2013.01); *A61M 25/0606* (2013.01); *A61M 2039/0036* (2013.01); *A61M 2039/064* (2013.01); *A61M 2039/0666* (2013.01)

(58) Field of Classification Search
CPC ...................... A61M 25/0097; A61M 25/0606; A61M 2039/0666; A61M 2039/0036; A61M 2039/064
USPC ............... 604/244–246, 167.02, 167.01, 256, 604/167.06; 251/30.02, 30.05
See application file for complete search history.

(56) References Cited

U.S. PATENT DOCUMENTS

| | | | |
|---|---|---|---|
| 4,781,693 A * | 11/1988 | Martinez et al. | 604/175 |
| 5,085,645 A * | 2/1992 | Purdy et al. | 604/167.03 |
| 5,211,634 A | 5/1993 | Vaillancourt | |
| 5,330,435 A * | 7/1994 | Vaillancourt | 604/167.01 |
| 5,697,914 A | 12/1997 | Brimhall | |
| 5,807,348 A * | 9/1998 | Zinger et al. | 604/246 |
| 5,810,780 A | 9/1998 | Brimhall et al. | |
| 5,843,046 A * | 12/1998 | Motisi et al. | 604/256 |
| 5,935,110 A | 8/1999 | Brimhall | |
| 6,224,569 B1 | 5/2001 | Brimhall | |
| 6,228,060 B1 | 5/2001 | Howell | |
| 6,273,869 B1 | 8/2001 | Vaillancourt | |
| 6,506,181 B2 | 1/2003 | Meng et al. | |
| 6,719,726 B2 | 4/2004 | Meng et al. | |
| 7,670,317 B2 | 3/2010 | Cindrich et al. | |
| 7,691,088 B2 | 4/2010 | Howell | |
| 7,798,994 B2 * | 9/2010 | Brimhall | 604/110 |
| 8,066,675 B2 | 11/2011 | Cindrich et al. | |
| 2006/0015071 A1* | 1/2006 | Fitzgerald | 604/168.01 |
| 2011/0160663 A1* | 6/2011 | Stout et al. | 604/122 |
| 2012/0022469 A1 | 1/2012 | Alpert | |

* cited by examiner

*Primary Examiner* — Nicholas Lucchesi
*Assistant Examiner* — Weng Lee
(74) *Attorney, Agent, or Firm* — Jeanne Lukasavage; Craig Metcalf; Kirton McConkie

(57) ABSTRACT

A septum is disclosed that can be utilized in a catheter assembly to selectively seal an opening in the catheter assembly. The septum has a tube portion and a plug portion. The plug portion has a slit extending through it. The septum can transition from a non-collapsed state to a collapsed state. When the septum is in a non-collapsed state, the plug portion is offset from the tube portion such that some of the length of the slit extends outward from the distal end of the tube portion. When the septum transitions to the collapsed state, the plug portion is moved inward into the internal cavity such that some of the length of the slit may or may not extend outward from the distal end of the tube portion.

18 Claims, 11 Drawing Sheets

LOW DRAG, HIGH PRESSURE SEPTUM

BACKGROUND OF THE INVENTION

The present invention relates to septa used in catheter and introducer needle assemblies. In medicine, such catheter and introducer needle assemblies are used to place a catheter properly into the vascular system of a patient. Once in place, catheters, such as intravenous (or "IV") catheters, may be used to infuse fluids including normal saline, medicinal compounds, and/or nutritional compositions (including total parenteral nutrition, or "TPN") into a patient in need of such treatment. Catheters additionally enable the removal of fluids from the circulatory system and the monitoring of conditions within the vascular system of the patient.

One type of commonly used catheter is an "over-the-needle" catheter that is mounted over an introducer needle with a sharp distal tip. The introducer needle cuts through the patient's skin and provides structural support to the catheter as it advances through the skin. The distal edge of the catheter grips the outside of the introducer needle to facilitate the insertion of the catheter through the skin along with the introducer needle. When a portion of the introducer needle is inserted into the target vessel, the catheter is slid over the introducer needle into place within the target vessel. Once placement of the catheter has been confirmed, the introducer needle may be withdrawn from the catheter assembly, leaving the catheter in place.

As blood begins to flow into the catheter adapter, a variety of seals or septa can be in place within the catheter adapter for preventing outflow of fluid from the catheter assembly. Such a septum may rely on an interference fit between the catheter assembly and the introducer needle assembly to create radial compression forces on the introducer needle intended to prevent the unwanted escape of blood between the septum and the introducer needle. The compression forces operating on the introducer needle can also function to close the septum and maintain the septum closed after the introducer needle is removed. The interference fit closing the septum after needle withdrawal can introduce frictional forces at the needle-septum interface. These frictional forces can create drag forces that resist needle extraction, making it difficult for medical personnel to remove the needle from the catheter assembly, particularly with one hand. Occasionally, the frictional force required to remove the needle can result in uncomfortable or painful movement or vibration of the catheter within the patient. It would thus be an improvement in the art to provide a septum that has a lower frictional force resisting needle extraction while still providing adequate sealing functionality.

SUMMARY OF THE INVENTION

Accordingly, the present invention provides a septum for use in catheter and introducer needle assemblies. The septum can provide a seal about the introducer needle prior to and during needle removal, as well as providing a seal about the proximal opening of the catheter assembly following needle extraction. The septum is configured to provide minimized drag during needle extraction, while still providing an effective seal against high pressures within the catheter assembly, such as those involved in high-pressure fluid injections. These features are achieved, at least in part, by offsetting the slit of the septum such that the radial compression forces from the catheter adapter are applied to the slit are primarily indirect forces. In this offset configuration, the frictional forces on the needle at the needle-septum interface are minimized, facilitating needle withdrawal.

To provide improved sealing function during high-pressure fluid injections, the septum can be further configured to transition to a collapsed state, generally after the introducer needle is removed, when a relatively high pressure is applied to the distal face of the septum. In these instances, the portion of the septum containing the slit, a plug portion, can be collapsed, at least partially, into a tube portion of the septum, which can increase the compressive force on the slit, maintaining the slit closed despite the high pressures. In this collapsed state, the septum can withstand high pressures within the catheter assembly without compromising the seal provided by the septum. Thus, the septum can serve as a low-drag, high pressure septum.

Accordingly, in some aspects of the invention, a septum is provided that can be utilized in a catheter assembly to selectively seal an opening in the catheter assembly. The septum has a tube portion and a plug portion. The plug portion has a slit extending through it. The septum can move from a non-collapsed state to a collapsed state. When the septum is in the non-collapsed state, the plug portion is offset from the tube portion such that some of the length of the slit extends outward from the distal end of the tube portion. When the septum is in a collapsed state, the plug portion is moved inwards into an internal cavity of the tube portion such that the length of the slit extending outward from the distal end of the tube portion is reduced.

In some implementations of the septum, the internal cavity can extend from a proximal end of the tube portion to the plug portion. The internal cavity can have a smaller cross-sectional area (taken perpendicular to a central axis of the tube portion) than the plug portion, such that the plug portion plugs the internal cavity when it is moved therein. Moreover, as the plug portion is moved into the internal cavity, it increases the compressive force on at least that portion of septum, which can improve the sealing capabilities of the septum. The plug portion of the septum can extend outwardly from a central portion of the distal end of the tube portion and can be surrounded by a portion of the distal end of the tube portion that forms an annular surface around the plug portion.

In some implementations of the septum, a first compressive force is applied to surfaces of the slit when the septum is in the non-collapsed state, but a second, greater compressive force is applied to the surfaces of the slit in the collapsed state, thus providing increased sealing capabilities around the slit, which can strengthen the septum's seal against high pressures. The septum can move from the non-collapsed state to the collapsed state in response to a threshold pressure on a distal face of the septum. This provides a seal against high pressures which might otherwise compromise the septum's seal. This threshold pressure can be greater than a pressure produced by withdrawing a needle through the slit in the plug portion, such that the septum is not collapsed during needle withdrawal.

In some implementations of the catheter assembly, one or more holes can be disposed through the sidewalls of the catheter adapter that extends between the inner lumen and the external environment. The one or more holes can be located along the inner lumen at one or more locations that are covered by the septum when the septum is in the non-collapsed state, and that are uncovered by the septum when in the collapsed state. In this configuration, when the internal pressure within the catheter adapter is sufficient to compress the septum backwards such that the one or more holes are exposed, this internal pressure can be reduced as fluids flow out the one or more holes.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

Some embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

As used herein the term "proximal" is used to denote a portion of a device that, during normal use, is nearest the user wielding the device and farthest from the patient. The term "distal" is used to denote a portion of a device which, during normal use, is farthest from the user wielding the device and closest to the patient.

Additionally, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

In portions of the Detailed Description below, the invention is described in connection with a peripheral IV catheter having an integrated extension tube. It is to be understood that the septum of the present invention may be used with various other catheter systems. For example, the invention may be applicable to standard peripheral IV catheters, extended dwell catheters that require the needle to be connected to the needle hub by a stylet, and other medical devices in which it is desirable to include a septum to regulate the flow of fluid into or out of a space.

Figure 1:
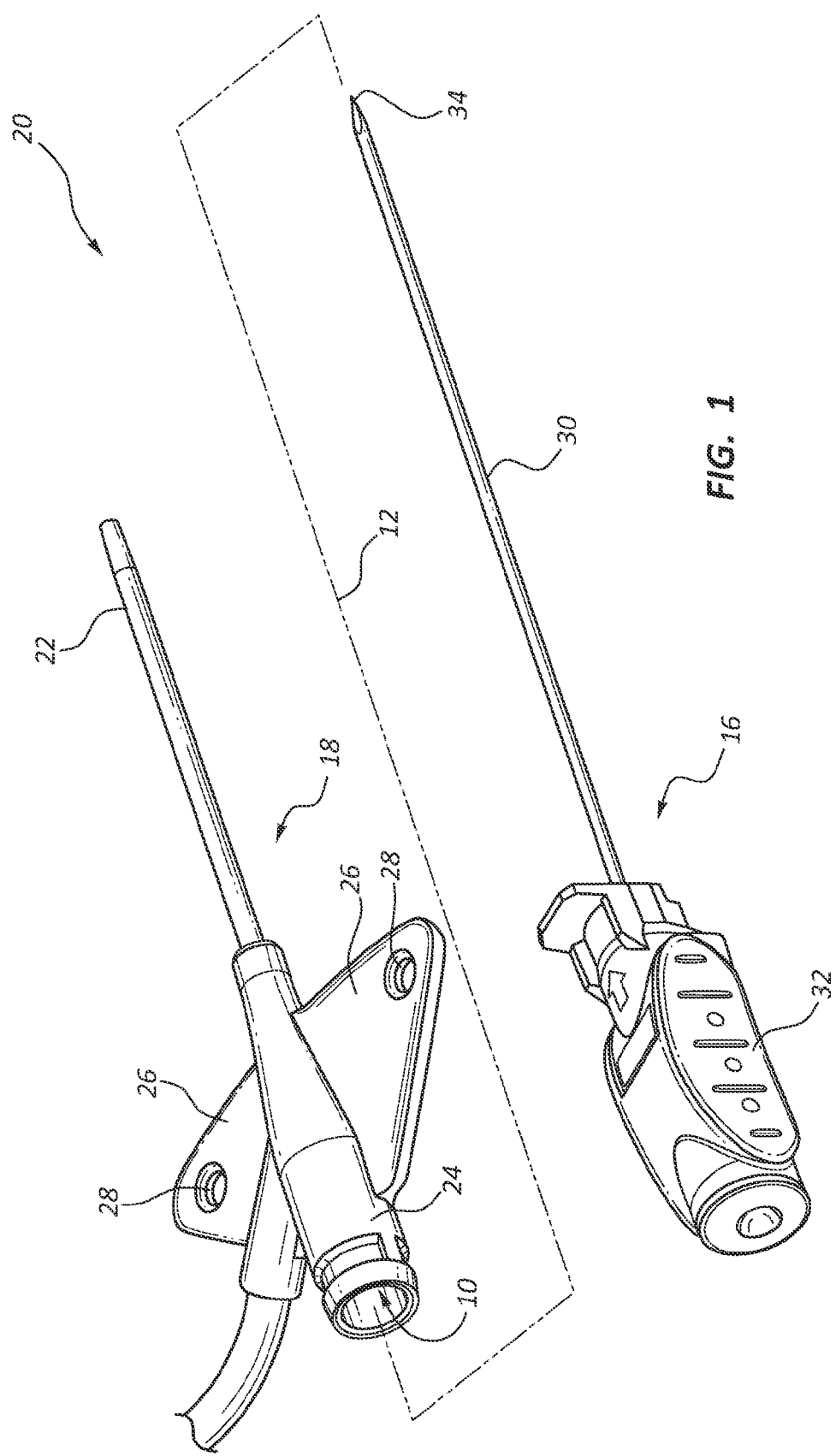
FIG. 1 is a partially exploded perspective view of a representative integrated catheter and introducer needle assembly incorporating a septum.

FIG. 1 generally illustrates an integrated catheter and introducer needle assembly 20 incorporating a septum 10 (disposed within the catheter adapter 24). The catheter and introducer needle assembly 20 can include a catheter assembly 18 including a catheter 22 attached to a catheter adapter 24, as well as a needle assembly 16 having an introducer needle 30. The introducer needle 30 can be inserted within the catheter assembly 18 along an axis 12, such as a longitudinal axis of the catheter assembly 18.

The catheter adapter 24 illustrated in FIG. 1 can include wings 26 that extend radially outwardly from either side of catheter adapter 24. The wings 26 can simplify handling of the catheter and introducer needle assembly 20 and provide greater surface area for attachment of the catheter 22 to the patient. The wings 26 may optionally include suture holes 28. The catheter adapter 24 can also include a septum 10 disposed therein that can at least partially prevent escape of fluid from the proximal end of the catheter adapter 24. The introducer needle assembly 16 can include an introducer needle 30. The proximal end of the introducer needle 30 is housed in a needle hub 32, while the distal end of the introducer needle 30 has a sharpened tip 34 for piercing the skin of a patient. In use, the introducer needle 30 and catheter 22 are inserted into a blood vessel of a patient, proper insertion is confirmed, and the introducer needle 30 is removed, leaving the catheter 22 in place.

Figure 2:
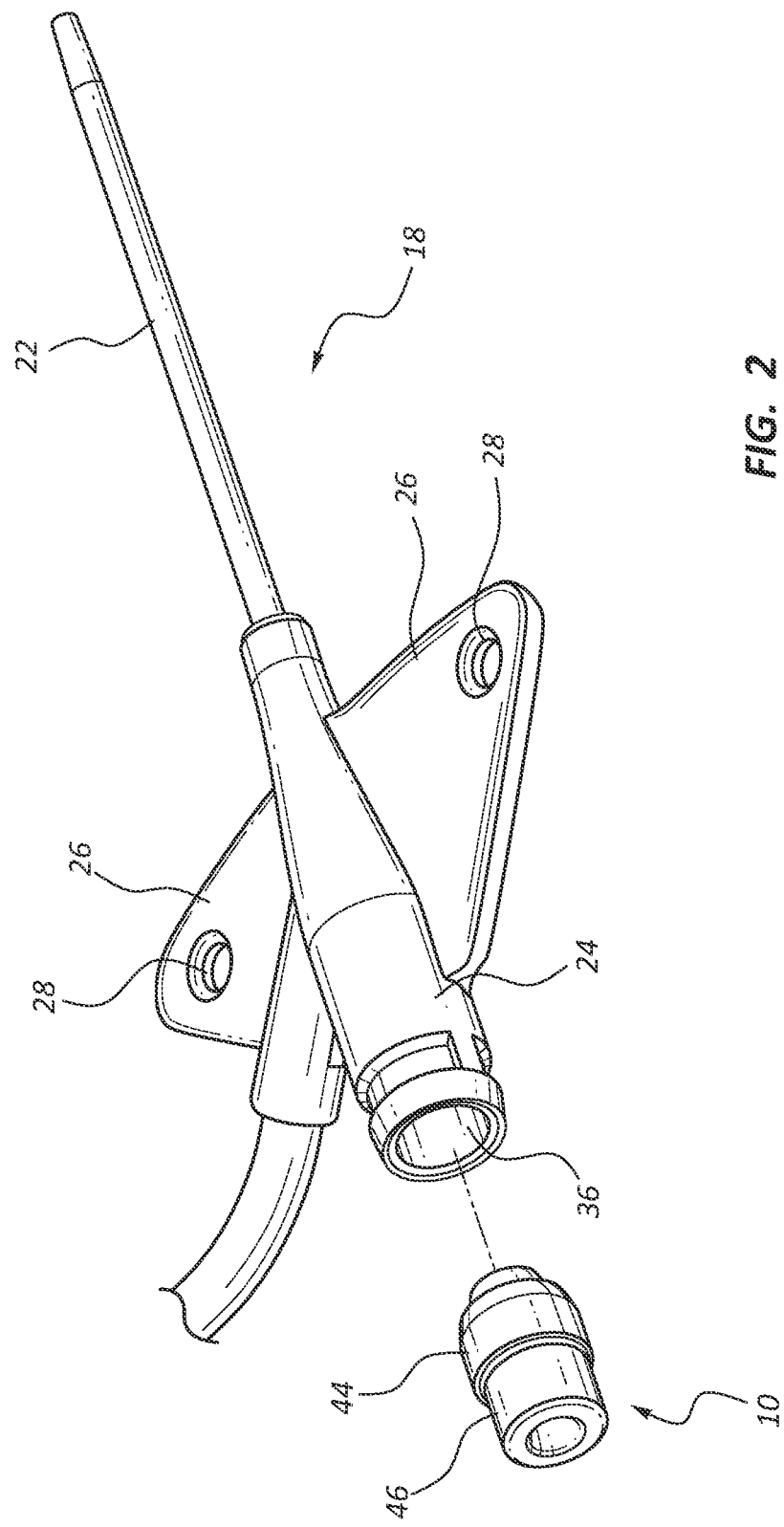
FIG. 2 is a partially exploded perspective view of the catheter assembly of FIG. 1 with the septum shown separated from the catheter assembly.

FIG. 2 is a partially exploded view of the catheter assembly 18 with the septum 10 shown separated from the catheter assembly 18. When assembled, the septum 10 can be positioned within the proximal portion of an inner lumen 36 of the catheter adapter 24 to prevent leakage of fluid from the proximal end of the catheter adapter 24. In some embodiments, the septum 10 is a one-piece device adapted to fit snuggly within the catheter adapter 24. For instance, the septum 10 can have an outer diameter that is about equal to or greater than the inner diameter of a portion of the inner lumen 36 of the catheter adapter 24 or a portion thereof.

As shown, the septum 10 can include surface features that assist to retain the septum 10 in place. For example, a proximal body portion 46 of the septum can have a reduced outer diameter, compared to the distal body portion 44, that is shaped and sized to compatibly fit within a sleeve (not shown) that assists to retain the septum 10 in place. The reduced outer diameter of the proximal body portion 46 can also compatibly fit around an inwardly oriented annular ring (not shown) on the inner surface of the inner lumen 36 of the catheter adapter 24. Other such representative structures used to retain the septum 10 in place are shown in FIGS. 6 through 10 and described below.

Figure 3:
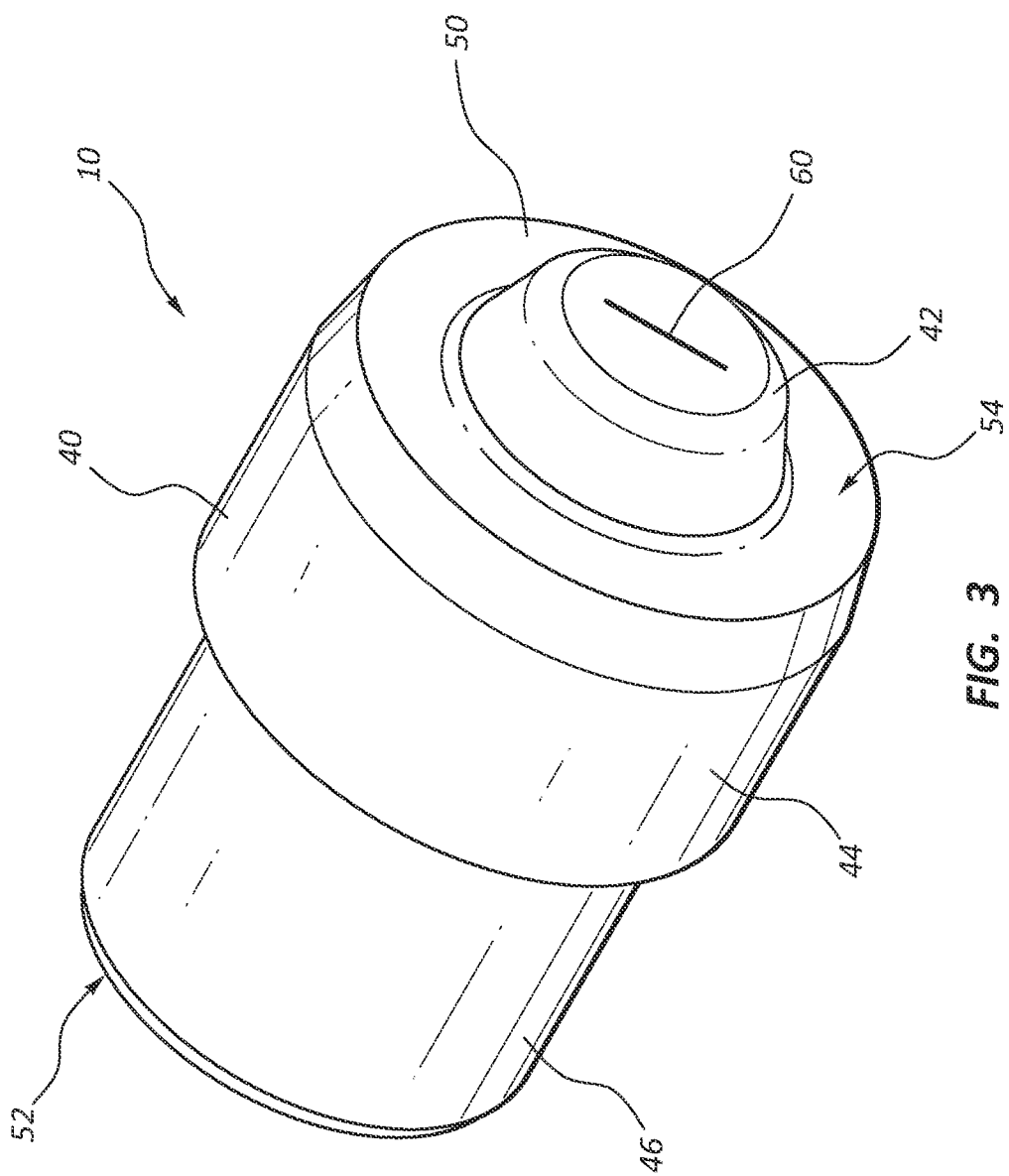
FIG. 3 is an isolated perspective view of a representative septum.

FIGS. 3 through 7 show isolated views of embodiments of the septum 10. Reference will first be made to FIG. 3, which depicts a perspective view of the septum 10. The septum 10 can be configured to provide a seal about the introducer needle 30 prior to and during needle removal of the catheter assembly 18. The septum 10 can be configured to provide a low drag force during needle extraction, while still providing an effective seal against high pressures within the catheter assembly 18, such as those involved in high-pressure fluid injections. These features can be achieved, at least in part, by offsetting the slit 60 of the septum 10 distally such that a primarily indirection radial compression force is applied to the majority of the slit 60 from the catheter adapter 24. In this offset configuration, the drag forces at the needle-septum interface are minimized during withdrawal of the introducer needle 30.

Figure 6:
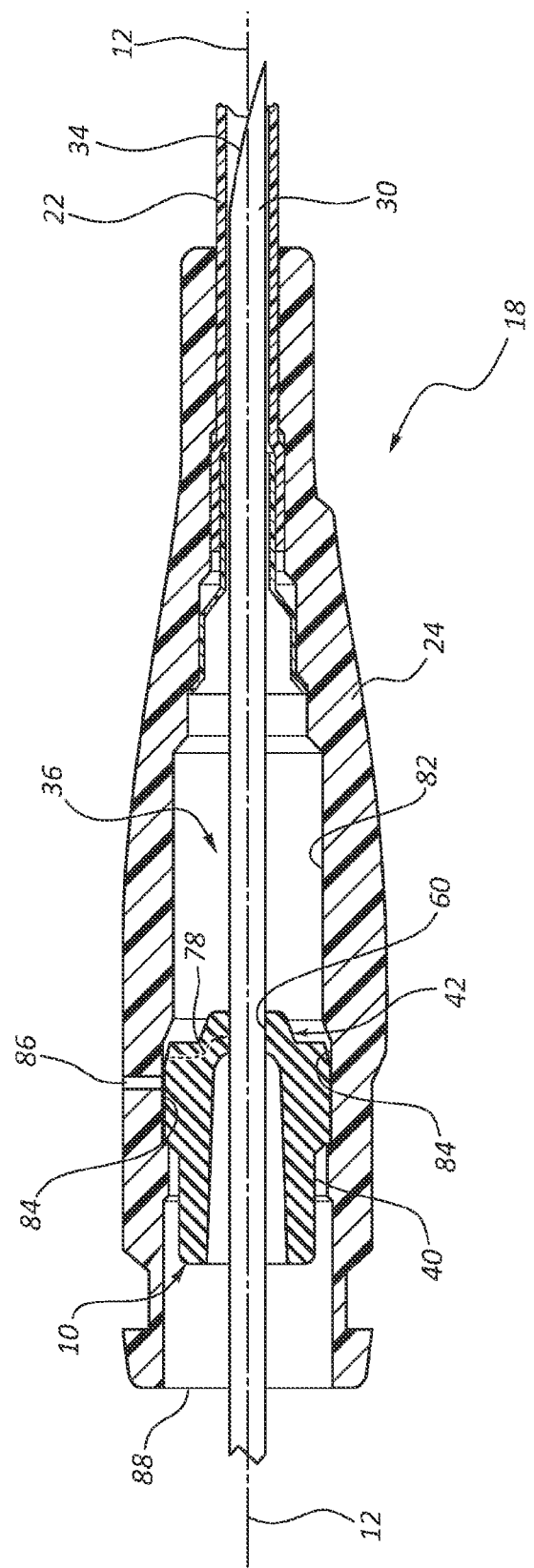
FIG. 6 is a cross-sectional view of a catheter assembly with an introducer needle in place.
Figure 7:
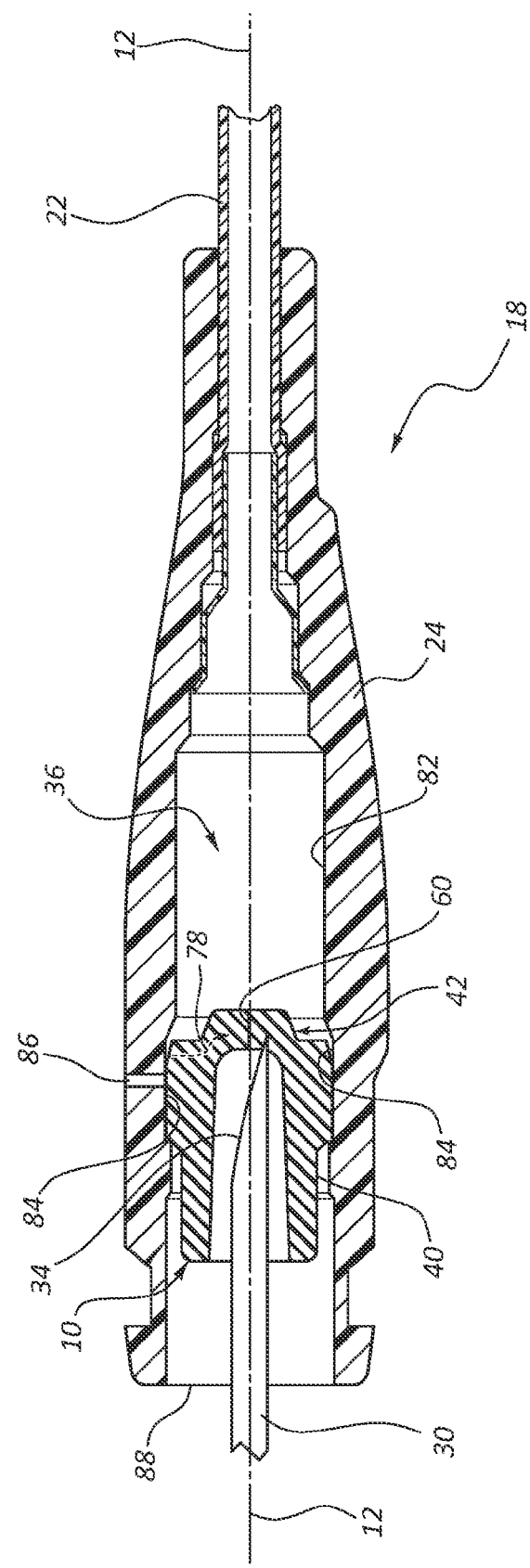
FIG. 7 is a cross-sectional view of the catheter assembly of FIG. 6 with the introducer needle partially removed and the septum in a non-collapsed state.
Figure 8:
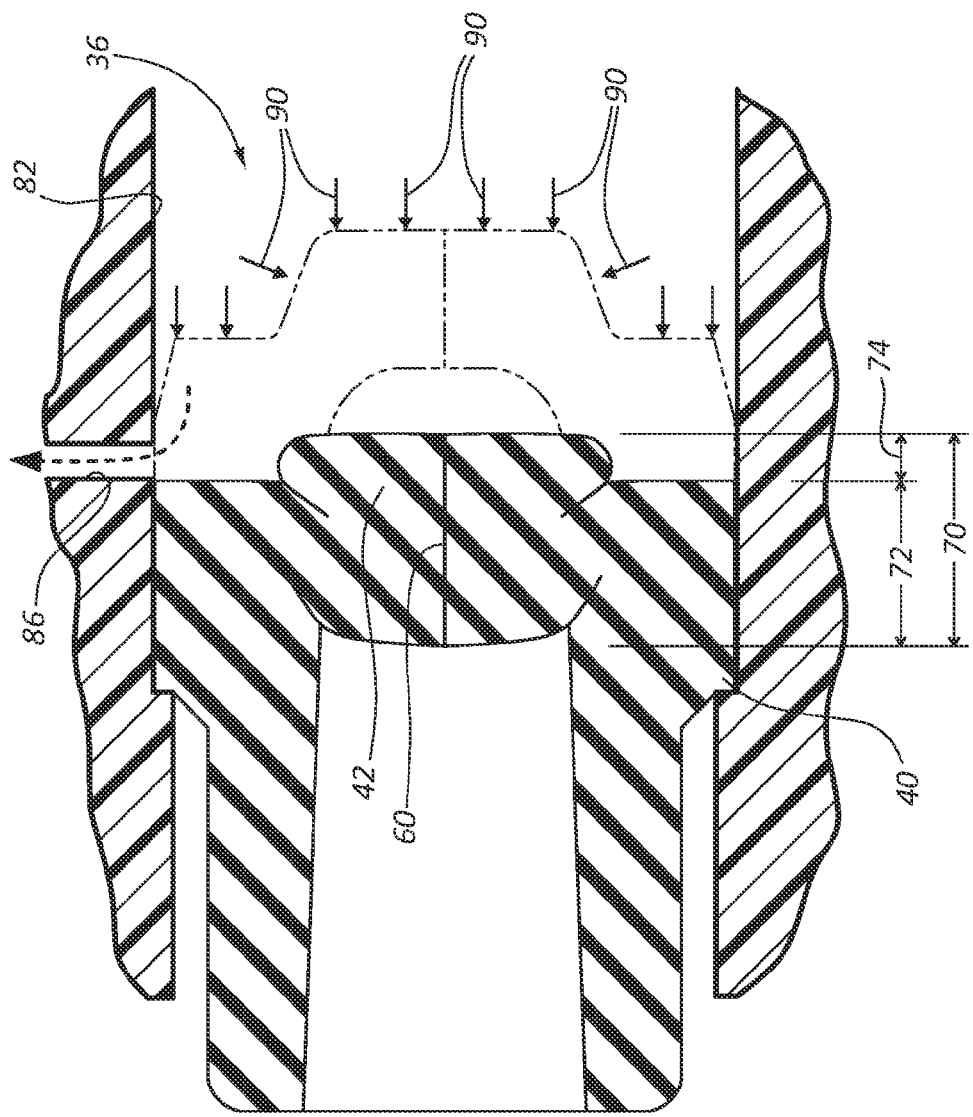
FIG. 8 is a cross-sectional view of the catheter assembly of FIG. 6 with the introducer needle removed and the septum in a collapsed state.

To provide improved sealing function during high-pressure fluid injections, the septum 10 can also be configured to transition from a non-collapsed state (as shown in FIGS. 3-7) to a collapsed state (as shown in FIG. 8), after the introducer needle 30 is removed and when a relatively high pressure is applied to the distal face 54 of the septum 10. In these instances, the portion of the septum 10 containing the slit 60, a plug portion 42, can move, at least partially, into a tube portion 40 of the septum 10, which can increase the compressive force on the slit 60, maintain the slit 60 closed. In this collapsed state, the septum 10 can be configured to withstand high pressures within the catheter assembly 18 without compromising the seal provided by the septum 10.

Reference will now be made to the septum 10 in a non-collapsed state, as shown in FIG. 3. As shown, in some configurations, the septum 10 can be a single-piece septum 10 that can generally include a tube portion 40 and a plug portion 42. The plug portion 42 can have a slit 60 extending through it along the central axis 12 of the septum 10. In this non-collapsed state, the plug portion 42 can be offset from the tube portion 40 in a manner in which some or all of the length (shown as element 70 in FIG. 5) of the slit 60 extends distally from the distal end 50 of the tube portion 40. The portion of the length 70 which extends distally can include about 15% to about 100% of the slit 60, including about 15%, about 20%, about 30%, about 40%, about 50%, about 60%, about 70%, about 80%, about 90%, and about 100% of the length 70 of the slit 60. As used herein the term "length of the slit" refers to the length of the slit 60 extending between the distal and the proximal ends of the plug portion 42. In some configurations, as shown, the plug portion 42 extends from a central portion of the distal end 50 of the tube portion 40, and the distal end 50 of the tube portion 40 can form an annular surface around the plug portion 42.

Figure 4:
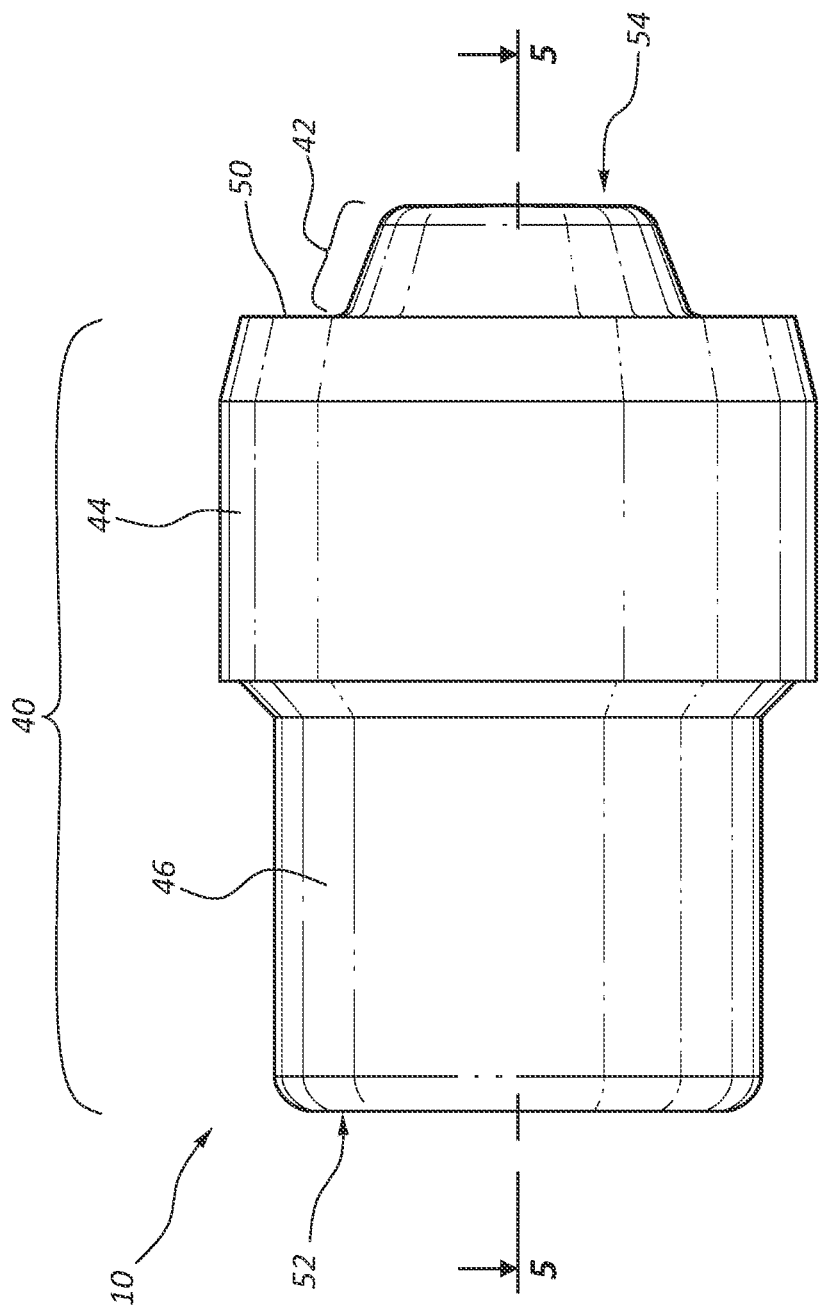
FIG. 4 is an isolated side view of the septum of FIG. 3.

FIG. 4 illustrates a side view of the septum 10 of FIG. 3 including the distal body portion 44, with its larger outer dimensions, and the proximal body portion 46, with its reduced outer dimensions. This figure also shows how the plug portion 42 extends distally outward from a central portion of the distal end 50 of the tube portion 40 of the septum 10. As further shown, one or more edges of the septum 10 can be rounded or tapered.

Figure 5:
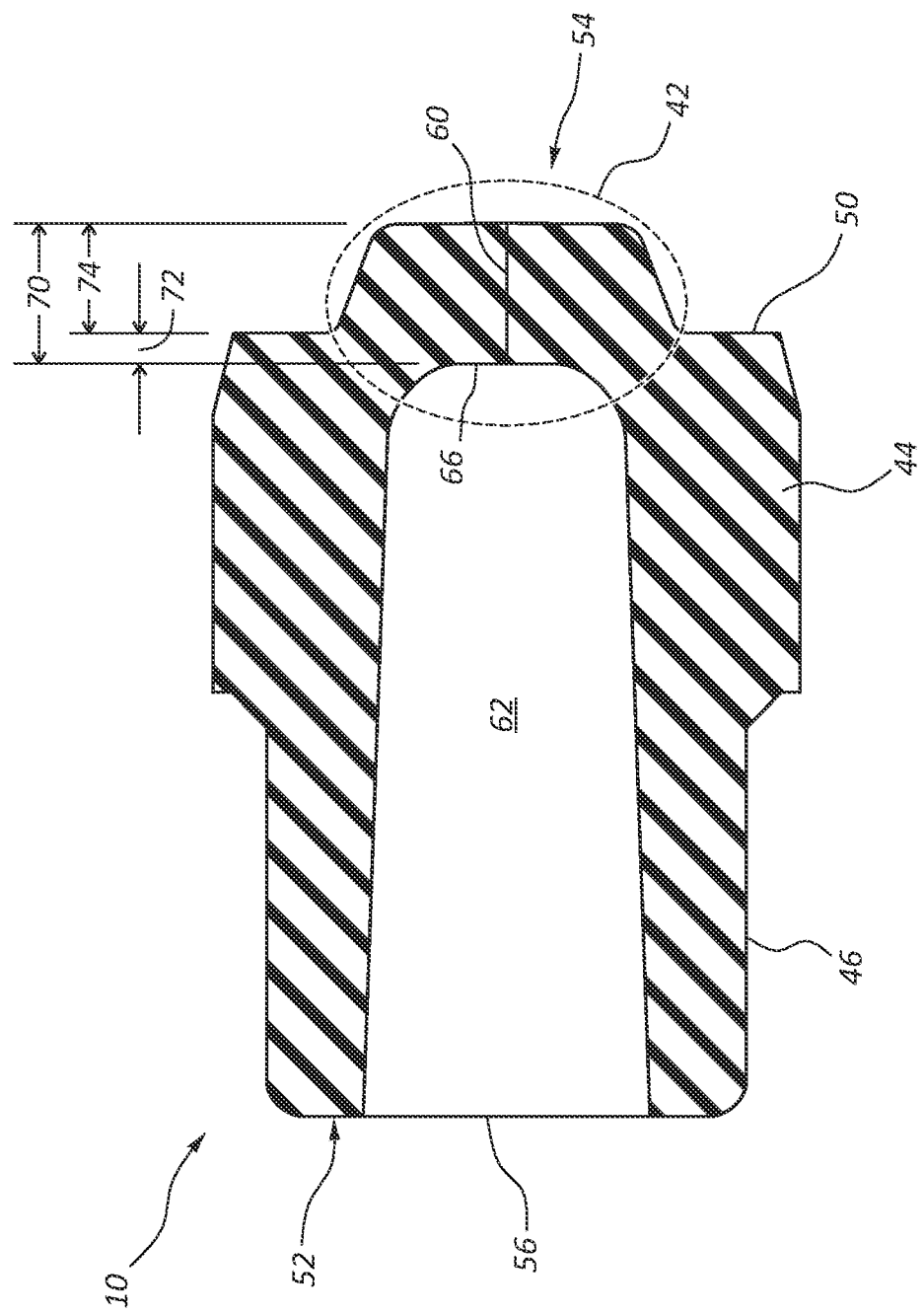
FIG. 5 is an isolated cross-sectional view of the septum of FIGS. 3 and 4 taken at line 5-5 of FIG. 4.

Reference will now be made to FIG. 5, which illustrates a cross sectional view of the septum 10 taken along line 5-5 of FIG. 4. As shown, in some configurations, the septum 10 can include an internal cavity 62 that extends from an opening 56 in proximal end 52 of the tube portion 40 to the plug portion 42. As such, the proximal side of the plug portion 42 can define the distal end 66 of the internal cavity 62. The internal cavity 62 can form an interior of at least a portion of (or a majority of) the tube portion 40 of the septum 10. In some embodiments, the internal cavity 62 can serve to provide a region where little of no pressure is placed on the portions of the introducer needle 30 located therein. The internal cavity 62 can also serve to provide a region into which the plug portion 42 of the septum 10 can collapse under high pressures, as shown in FIG. 8 and describe below.

FIG. 5 further depicts the plug portion 42, which is substantially designated by an oval for clarification. Plug portion 42 is offset from the tube portion 40 such that some (e.g., at least about one-half) of the length 70 of the slit 60 extends distally from the distal end 50 of the tube portion 40. For instance, the portion 74 of the length 70 of the slit 60 that extends distally from the distal end 50 of the tube portion 40 (which is referred to herein as the offset length 74 or offset portion 74) can be (but does not have to be) greater than the portion 72 of the length of the slit 60 that is located proximally from the distal end 50 (which is referred to herein as the overlapping length 72 or overlapping portion 72). This offsetting results in the forces applied on the septum 10 from a catheter adapter 24 being primarily indirect, radial compression forces. The primarily indirect, radial compression forces are not as strong as otherwise direct compression forces, and thus result in reduced contact force at the needle-septum interface and lower drag forces on the introducer needle 30 during needle extraction. This can make it easier for medical personnel to remove the introducer needle 30 from the catheter assembly 24, particularly with one hand. The reduced contact force at the needle-septum interface can also reduce or eliminate any uncomfortable movement or vibration caused by withdrawing the introducer needle 30 from the patient through the septum 10.

Reference will now be made to FIG. 6, which illustrates a septum 10 installed within a catheter assembly 18. The septum 10 can be positioned along a longitudinal axis 12 within an inner lumen 36 of the catheter adapter 24. The inner lumen 36 can extend along the longitudinal axis 12 of the catheter assembly 18 between the proximal and distal ends of the catheter adapter 24 and into and through the catheter 22. The inner lumen 36 can have one or more recesses 84 formed on its inner surface 82 that can be shaped and sized to retain at least a portion of the outer surface of the septum 10, and at least partially prevent the septum 10 from being forced out the proximal opening 88 of the inner lumen 36 when the internal pressure of the inner lumen 36 is increased. In some configurations, one or more holes 86 are formed in the sidewall of the catheter adapter 24, as will be described below.

In some embodiments, the inner lumen 36 of the catheter adapter 24, along with the tube portion 40 of the septum 10, can be shaped and sized such that an inward compressive force is applied on the tube portion 40 of the septum 10 from the catheter adapter 24. This inward compressive force, as described above, can act on the slit 60, maintaining it closed against the introducer needle 30 and later closed without the introducer needle 30. As previously noted, because the slit 60 is partially offset from the tube portion 40, the compression forces acting on some of the slit 60 are indirect, following an indirect compression path 78.

Referring still to FIG. 6, during storage and use of the catheter adapter 24, the plug portion 42 of the septum 10 can conform to the shape of the introducer needle 30. Thus, as the catheter 22 and introducer needle 30 are inserted into a patient, the septum 10 prevents leakage of fluid flowing into the catheter adapter 24. Once the introducer needle 30 has been removed, however, as illustrated in FIG. 7, the slit 60 of the septum 10 closes to seal the catheter adapter 24. In FIG. 7, the slit 60 is shown to have closed as the distal tip 34 of the introducer needle 30 is removed into the internal cavity 62 of the septum 10. During any subsequent fluid infusion through the catheter assembly 18, the plug portion 42 of the septum 10, which protrudes slightly into the flow path of the infusant, can create a disturbance in the flow which may results in improve flushing ability within the catheter adapter 24.

Reference will now be made to FIG. 8, which shows the transition of the septum 10 from a non-collapsed state to a collapsed state in response to hydrostatic pressures 90 on the distal face 54 of the septum 10. The exterior shape of the septum 10 in a non-collapsed state is depicted using broken lines, while the shape of the septum 10 in the collapsed state is shown using solid lines. As shown, in response to pressure on the distal face 54 of the septum 10, such as the pressure created during a high-pressure fluid infusion, the septum 10 can collapse to a collapsed state. To ensure that the septum 10 does not collapse during needle withdrawal, the septum 10 can be configured to collapse under pressures that exceed a threshold value, which is greater that the pressure value caused during needle withdrawal through the slit 60.

As shown, when the septum 10 is in a collapsed state, the plug portion 42 is moved proximally into the internal cavity 62 of the septum 10 such that the length 70 of the slit 60 moved proximally from the distal end 50 of the tube portion 40. Accordingly, in this state, the offset length 74 of the slit 60 is reduced and the overlapping length 72 of the slit 60 is increased. In some instances, in this collapsed state, the portion of the length 70 which extends distally can include about 0% to about 75% of the slit 60, including about 5%, about 10%, about 20%, about 30%, about 40%, about 50%, about 60%, about 70%. In some configurations, about 50% of the slit 60 extends distally in the uncompressed state, while about 20% of the slit extends distally in the compressed state. Moreover, since less of the slit length 70 is offset from the tube portion 40, the compressive force on the surface of the slit 60 are greater in this state because these compressive forces act directly, rather than indirectly, on the surfaces of the slit 60. Furthermore, when the plug portion 42 is larger than the internal cavity 62, the plug portion 42 is compressed into the internal cavity 62, creating additional compressive forces that act on the slit 60. In some instances, as the hydrostatic pressures 90 increases, the plug portion 42 can be wedged even deeper within the internal cavity 62, thus increasing the compressive forces on the slit 60, further strengthening of the seal against the increased pressure.

In some embodiments, the septum 10 can be configured such that in both the collapsed and non-collapsed states, absent something being inserted through the slit 60, the surfaces of the slit 60 are maintained in contact. In other words, the slit 60 remains closed. Accordingly, the plug portion 42 can be shaped and sized to be large enough that it is resistant to being blown into the interior cavity 62 under the hydrostatic pressure, thus opening the slit 60. Accordingly, the plug portion 42, can be larger than the internal cavity 62, so that the plug portion 42 does not completely snap through as it is forced into the internal cavity 62, during which time the tube portion 40 may fold in around the plug portion 42. This strengthens the overall sealing ability of the septum 10. Thus, in some configurations, the cross sectional area of the internal cavity 62 (taken perpendicular to a central axis 12 of the tube portion 40) is smaller than the cross-sectional area of the plug portion 42 (also taken perpendicular to the central axis 12 of the tube portion 40) taken at a location distal the distal end 50 of the tube portion 40. This difference in size can cause the plug portion 42 to plug the internal cavity 62 when the septum 10 is in the collapsed state, while permitting the slit 60 to remain closed.

As shown in FIGS. 6 through 8, in some embodiments, one or more holes 86 can be strategically formed through the sidewall of the catheter adapter 24 to provide pressure relief to the catheter adapter 24 when the septum 10 is in the collapsed state and the septum 10 is compressed proximally to the point that the one or more holes 86 are exposed. These holes 86 could reduce the potential for pressure spikes that may otherwise jeopardize the integrity of the components of the catheter assembly 18 or damage the patient's veins. In some configurations, after some pressure is relieved, the septum 10 could recover from its compressed state and re-cover the holes 86. Accordingly, the one or more holes 86 can be location between the septum 10 and the inner surface 82 of the inner lumen 36 when the septum 10 is in the non-collapsed stated, but which can be uncovered when the septum 10 is pushed back, proximally, by a pressure level that exceeds a threshold pressure. In some embodiments, two or more holes 86 are located in the catheter adapter 24 at different distances along the longitudinal axis 12 of the catheter assembly 18, such that the farther the septum 10 is forced proximally, the more holes 86 become exposed making more pressure relief available. In some embodiments, multiple holes 86 are disposed along each location along the longitudinal axis 12 of the catheter assembly 18, such that as fluid is ejected from the holes 86, the lateral forces generated from the escaping fluid are counteracted, thus preventing undesired movement of the catheter adapter.

Figure 9:
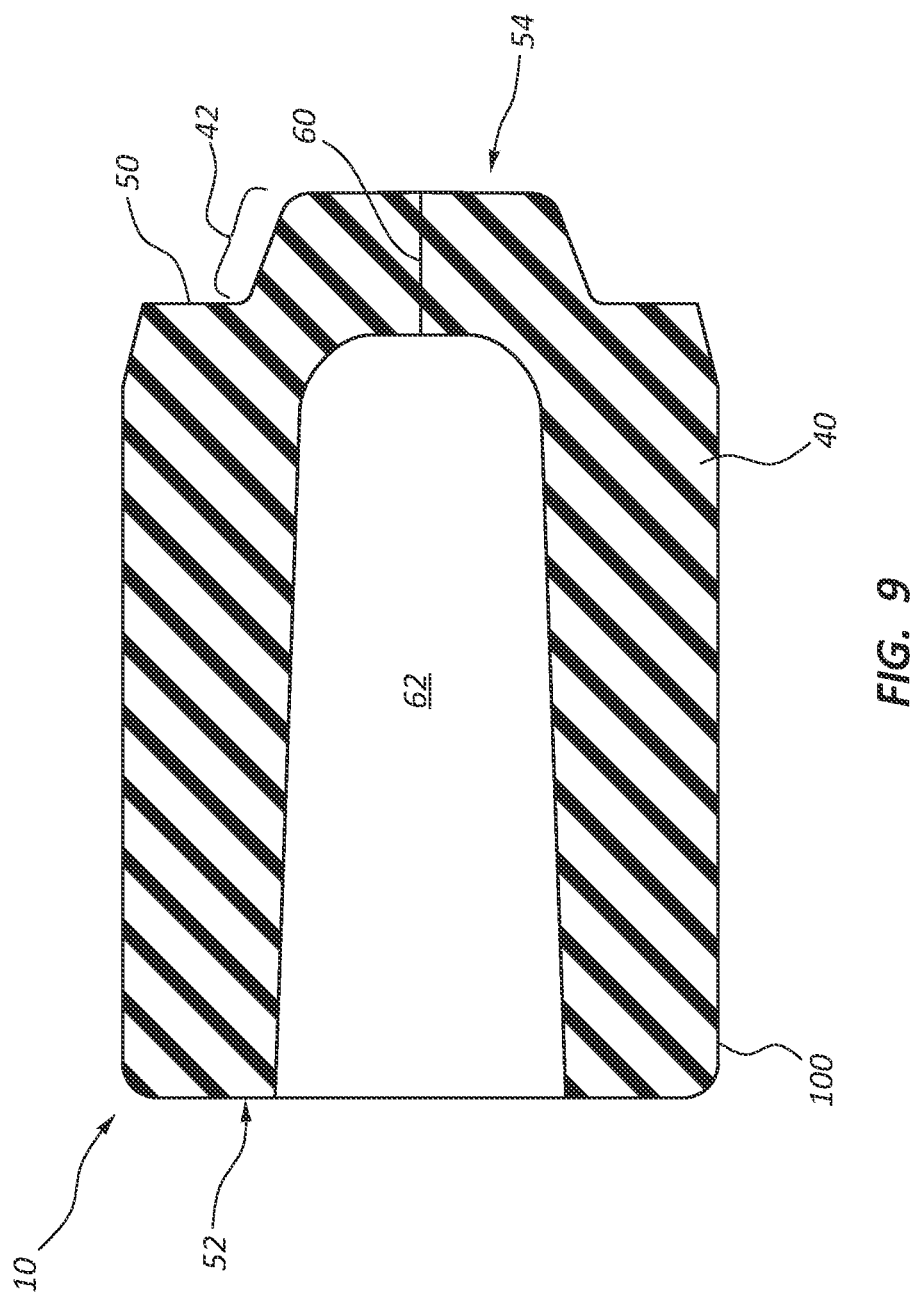
FIG. 9 is an isolated cross-sectional view of another embodiment of a septum.
Figure 10:
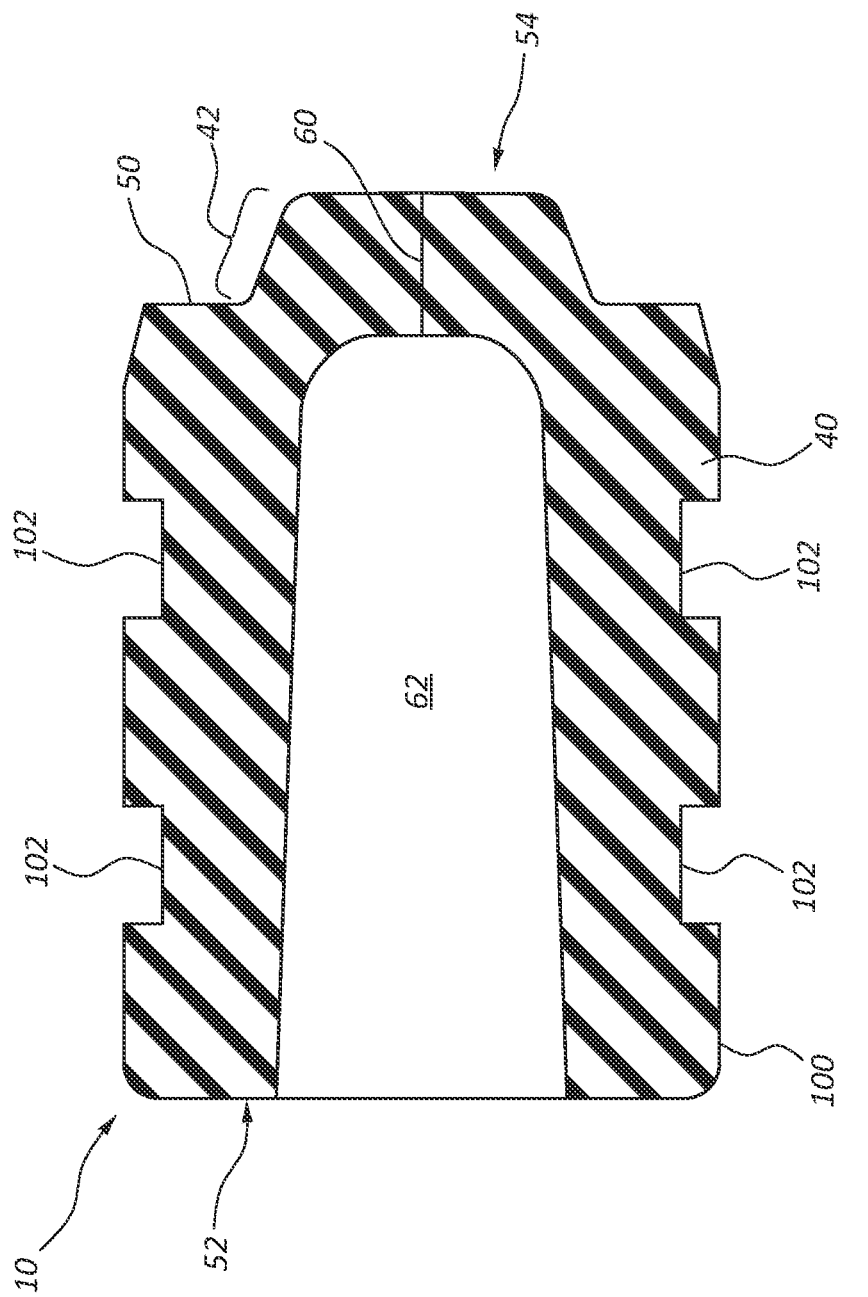
FIG. 10 is an isolated cross-sectional view of yet another embodiment of a septum.

FIGS. 9 and 10 show embodiments of septa 10 having alternative exterior surface configurations. Turning first to FIG. 9, in some embodiments, the exterior surface 100 of the tube portion 40 of the septum 10 is substantially cylindrical, with no recesses or protrusions, along substantially the entire length of the body 40. Turning now to FIG. 10, in some configurations of the septum 10, the exterior surface 100 of the tube portion 40 of the septum 10 is substantially cylindrical and includes one or more recesses 102 that can compatibly receive one or more annular rings on the inner surface 82 of the inner lumen 36 of the catheter adapter 24. In other configurations, the exterior surface 100 of the tube portion 40 of the septum 10 includes one or more annular rings that can be compatibly received with one or more recesses in the inner surface 82 of the inner lumen 36 of the catheter adapter 24. It is further contemplated that various other features and surface configurations can be formed on the outer surfaces of the septum 10.

Figure 11:
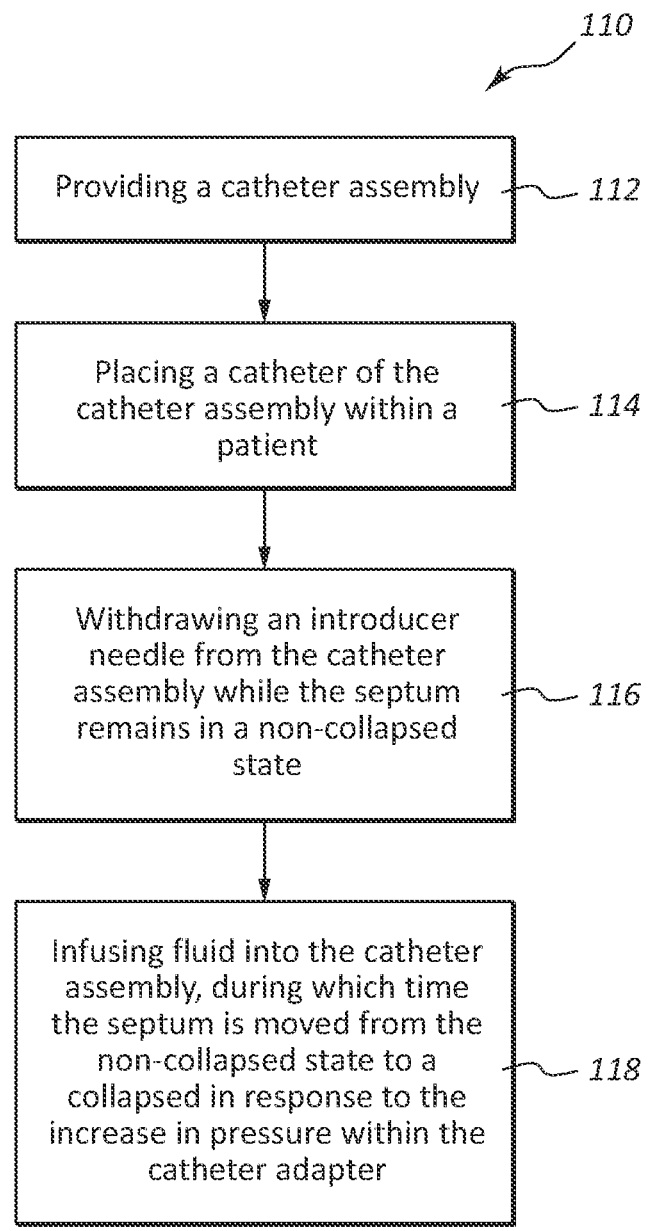
FIG. 11 is a flowchart of a method of sealing a catheter assembly.

Reference will now be made to FIG. 11, which illustrates a flowchart of a method 110 for using the needle and catheter assemblies 20. In step 112, a catheter assembly 18 is provided. The catheter assembly 18 can include a catheter adapter 24 having an inner lumen 36 extending therethrough and an introducer needle 30 extending through the inner lumen 36. A septum 10 can be provided within the inner lumen 36 of the catheter adapter 24 that is disposed about the introducer needle 30. The septum 10 can have a tube portion 40 and a plug portion 42 that is coupled to a distal end of the tube portion. A slit 60 can extend through the septum 10. The septum 10 can transition from a non-collapsed state, in which some of a length 70 of the slit 60 extends distally from the distal end of the tube portion 40, to a collapsed state, in which less or none of the length 70 of the slit 60 extend distally from the distal end 50 of the tube portion 40. Moreover, the septum 10 can transition from the non-collapsed state to the collapsed state in response to a pressure on a distal face 54 of the septum 10 exceeding a threshold value, the threshold value of pressure being greater than that produced by withdrawing the introducer needle 30 through a slit 60 in the plug portion 42.

In step 114, the catheter 22 of the catheter assembly 18 is placed in a blood vessel of a patient. At this stage, proper catheter insertion can be confirmed. Next, in step 116, the introducer needle 30 is withdrawn from the catheter assembly 18, while the septum 10 remains in the non-collapsed state.

The septum 10 can remain in this state during needle extraction because it can be configured to collapse under a pressure on its distal face 54 that exceeds the pressure created during needle withdrawal. Furthermore, in some configurations, the introducer needle 30 and slit 60 can include a lubricant, as known in the art, which can reduce needle drag.

In step 118, after the catheter 22 is in place, fluid may be infused into the patient through the catheter adapter 24 and catheter 22. The fluid can include normal saline, medicinal compounds, and/or nutritional compositions (including TPN). During fluid infusion, if the pressure within the catheter adapter 24 exceeds a threshold amount, the septum 10 can transition from the non-collapsed state to the collapsed state in response to pressure within the catheter adapter 24. Thus, the septum 10 can function both as a low-drag septum, and a high-pressure septum 10.

In view of the foregoing, it will be understood that using the catheter assemblies 18, septa 10, and methods of the present invention can provide various advantages and benefits. For instance, a septum 10 can provide a seal about the introducer needle 30 during use prior to and during needle removal. The septum 10 can also provide a seal about the proximal opening 88 of the catheter assembly 18 during use of the catheter assembly 18. The septum 10 further can be configured to apply a low drag force on the introducer needle 30 during needle extraction. Moreover, the septum 10 can respond to hydrostatic pressure 90 on the distal face 54 of the septum 10, which might otherwise compromise the seal, by deforming in a manner that is self-sealing and which strengthens the septum's sealing abilities. When deformed, or collapsed, the geometry of the septum 10 can be such that the plug portion 42 acts like a plug, which, when pressure is applied, is forced into a constricted region of the internal cavity 62 of the septum 10, thus energizing the slit seal in proportion to the pressure level. This plug action can also increase the contact force at the septum-catheter adapter interface, which also can improve that sealing surface in proportion to the pressure level.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A septum comprising:
   a tube portion having an internal cavity therein; and
   a plug portion coupled to a distal end of the tube portion having a non-collapsed state and a collapsed state, the plug portion having a slit extending therethrough, the slit having a slit length extending between a distal end of the plug portion and a proximal end of the plug portion, the plug portion being offset from the tube portion such that when the septum is in the non-collapsed state some of the length of the slit extends distally from the distal end of the tube portion, when the septum transitions to the collapsed state the plug portion is moved proximally into the internal cavity such that less of the length of the slit extends distally from the distal end of the tube portion and such that, when in the collapsed state, the tube portion applies an inward radial force against the plug portion to thereby seal the slit to prevent a fluid from passing through the slit.

2. The septum of claim 1, wherein the septum transitions from the non-collapsed state to the collapsed state in response to a pressure on a distal face of the septum that exceeds a threshold pressure.

3. The septum of claim 2, wherein the threshold pressure is greater than a pressure produced by withdrawing an introducer needle through the slit in the plug portion.

4. The septum of claim 1, wherein the plug portion extends from a central portion of the distal end of the tube portion.

5. The septum of claim 4, wherein the distal end of the tube portion forms an annular surface around the plug portion.

6. The septum of claim 1, wherein the internal cavity extends from a proximal end of the tube portion to the plug portion.

7. The septum of claim 1, wherein the internal cavity has a first cross sectional area, taken perpendicular to a central axis of the tube portion, that is smaller than a second cross-sectional area of the plug portion, taken perpendicular to the central axis of the tube portion at a location distal from the distal end of the tube portion.

8. The septum of claim 1, wherein the septum is a one-piece, elastomeric septum.

9. A catheter assembly, comprising:
   a catheter adapter having an inner lumen;
   a septum disposed within the inner lumen of the catheter adapter, the septum being able to transition from a non-collapsed state to a collapsed state;
   a tube portion of the septum having a proximal end and a distal end, the tube portion forming an internal cavity; and
   a plug portion of the septum coupled to the distal end of the tube portion, the plug portion having a slit extending therethrough, the slit having a slit length, the plug portion being offset from the tube portion such that when the septum is in the non-collapsed state some of the length of the slit extends distally from the distal end of the tube portion, when the septum is in the collapsed state, the plug portion is moved proximally into the internal cavity such that less of the length of the slit extends distally from the distal end of the tube portion and such that, when in the collapsed state, the tube portion applies an inward radial force against the plug portion to thereby seal the slit to prevent a fluid from passing through the slit.

10. The catheter assembly of claim 9, wherein a diameter of the internal cavity is smaller than a diameter of the plug portion such that when the plug portion is moved proximally into the internal cavity, the plug portion is compressed within the internal cavity thereby creating the inward radial force that seals the slit.

11. The catheter assembly of claim 10, wherein the inner lumen of the catheter adapter has a circular cross-sectional area.

12. The catheter assembly of claim 9, wherein, when in the collapsed state, less than 50% of the length of the slit extends distally from the distal end of the tube portion.

13. The catheter assembly of claim 9, wherein the internal cavity has a first cross sectional area, taken perpendicular to a central axis of the tube portion, that is smaller than a second cross-sectional area of the plug portion, taken perpendicular to the central axis of the tube portion at a location distal from the distal end of the tube portion.

14. The catheter assembly of claim 9, wherein the septum transitions from the non-collapsed state to the collapsed state in response to a pressure on a distal face of the septum exceeding a threshold pressure.

15. The catheter assembly of claim 14, wherein the threshold pressure is greater than a pressure produced by withdrawing an introducer needle through the slit.

16. The catheter assembly of claim 9, further comprising one or more holes disposed through the catheter adapter between the inner lumen of the catheter adapter and the external environment, the one or more holes being disposed at one or more locations along the inner lumen that are covered by the septum when in the non-collapsed state and that are uncovered by the septum when in the non-collapsed state.

17. A method of sealing a catheter assembly, the method comprising:

providing a catheter assembly having a catheter adapter, a catheter, and a septum, the septum being disposed in a non-collapsed state within the catheter adapter, the catheter assembly further having an introducer needle extending through the septum, wherein the septum includes a tube portion forming an internal cavity and a plug portion coupled to a distal end of the tube portion, the plug portion having a slit extending therethrough, the slit having a slit length, the septum being movable from the non-collapsed state, in which some of the length of the slit extends distally from the distal end of the tube portion, to a collapsed state, in which the plug portion is moved proximally into the internal cavity such that less of the length of the slit extends distally from the distal end of the tube portion and such that, when in the collapsed state, the tube portion applies an inward radial force against the plug portion to thereby seal the slit to prevent a fluid from passing through the slit;

placing the catheter within a patient;

withdrawing the introducer needle from the catheter assembly while the septum remains in the non-collapsed state; and infusing fluid into the catheter assembly, during which time the septum transitions from the non-collapsed state to the collapsed state in response to an increase in pressure within the catheter adapter.

18. The method of claim 17, wherein, one or more holes disposed through the catheter adapter between the inner lumen of the catheter adapter and the external environment are exposed when the septum transitions to the collapsed state.

* * * * *